United States Patent [19]

Schinkel et al.

[11] Patent Number: 5,195,979
[45] Date of Patent: Mar. 23, 1993

[54] SET OF INSTRUMENTS FOR THE UTERINAL EMBRYO TRANSFER AND INTRA-UTERINE INSEMINATION

[75] Inventors: Otto Schinkel, Bovenden; Josef Hervath, Göttingen, both of Fed. Rep. of Germany

[73] Assignee: Labotect-Labor-Technik Gottinger GmbH, Gottingen, Fed. Rep. of Germany

[21] Appl. No.: 814,410

[22] Filed: Dec. 24, 1991

[30] Foreign Application Priority Data

Jun. 25, 1991 [DE] Fed. Rep. of Germany ....... 9107792

[51] Int. Cl.⁵ .............................................. A61M 5/178
[52] U.S. Cl. ...................................... 604/164; 604/906
[58] Field of Search ............... 604/282, 198, 263, 117, 604/906, 164, 165

[56] References Cited

U.S. PATENT DOCUMENTS

| 2,740,404 | 4/1956 | Kohl | 604/198 X |
| 3,406,687 | 10/1968 | Moyer | 604/117 |
| 4,136,695 | 1/1979 | Dafoe | 604/198 |
| 4,760,847 | 8/1988 | Vaillancourt | 604/117 X |

Primary Examiner—John D. Yasko
Attorney, Agent, or Firm—Hopkins & Thomas

[57] ABSTRACT

Set of instruments for uterine embryo transfer and intra-uterine insemination having a catheter guide tube (1) and a cather (8) provided with a metal reinforcing tube (11) in its proximal area. The catheter guide tube (1) has a gentle bend (2) in its distal area and ends in a ball (3) at its distal end. The metal reinforcing tube (11) surrounds the catheter (8).

10 Claims, 3 Drawing Sheets

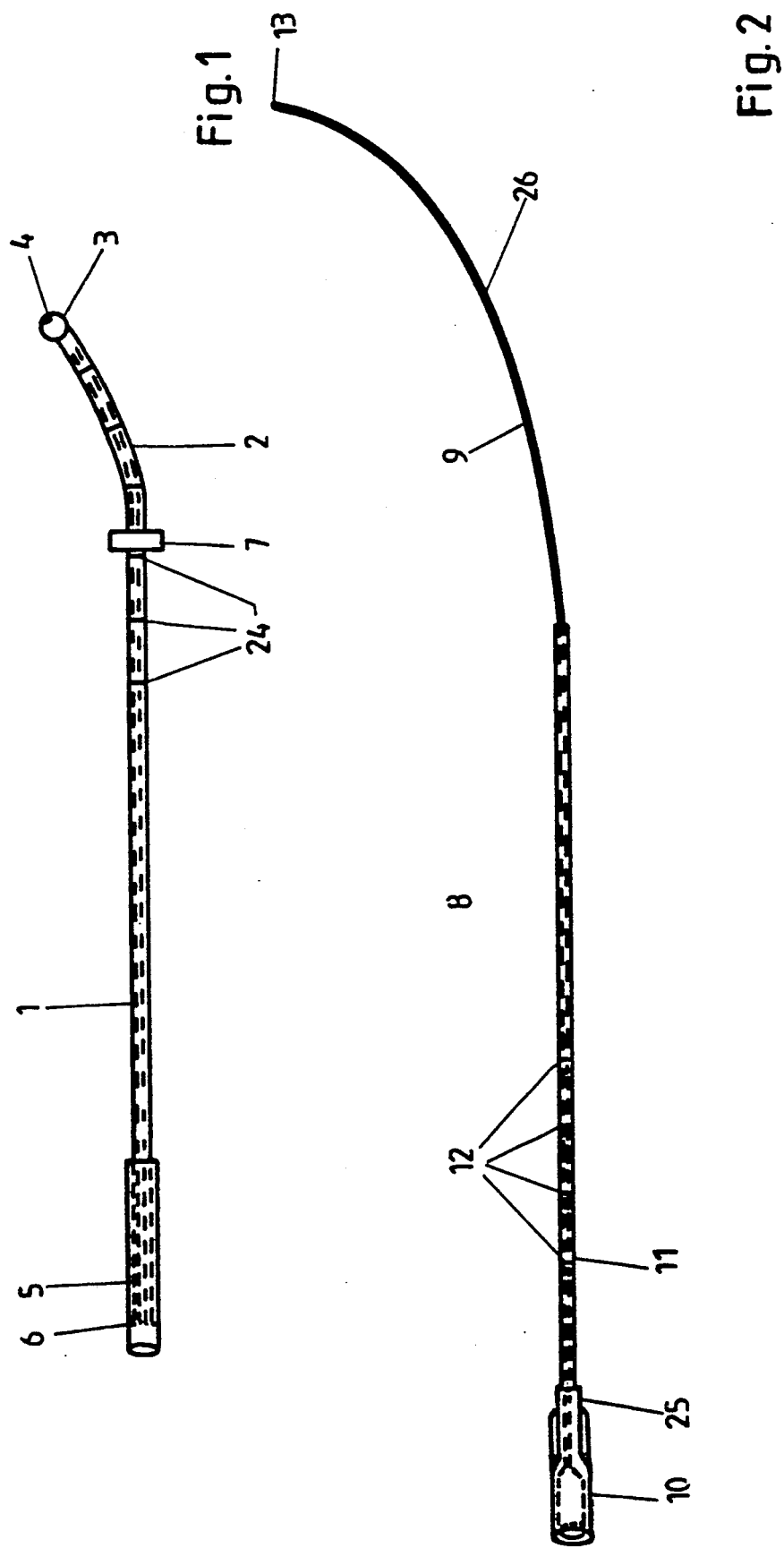

SET OF INSTRUMENTS FOR THE UTERINAL EMBRYO TRANSFER AND INTRA-UTERINE INSEMINATION

FIELD OF THE INVENTION

The invention refers to a set of instruments for uterine embryo transfer and intra-uterine insemination using a catheter guide tube and catheter provided with a metal reinforcing tube in its proximal area. Such a set of instruments is used if egg cells fertilized in vitro are transferred into the uterus after, as a rule, two cell divisions, or if sperm cells are introduced into the uterus.

BACKGROUND OF THE INVENTION

A set of intruments of the aforementioned type is known. It has a straight catheter guide tube rounded off at its distal end. The interior of the reinforcing tube for the associated catheter is constructed so that it forms the inner surface of the straight catheter in the proximal area. Upon insertion into the uterus, this known, one-piece, flexible catheter guide tube, made from synthetic material, is stabilized by a metal mandrin. This mandrin shapes the uterus prior to inserting the catheter guide tube so that insertion is made easier. Of course, the catheter guide tube only maintains this shape as long as the mandrin is located inside the tube. The reinforcing tube prevents the catheter from bending through the effect of the weight of a syringe placed in the connection for the syringe on the catheter. It has been shown that a disadvantage of this known set of instruments is that upon introducing the catheter guide tube into the uterus, it is almost impossible to avoid injuring the endometrium. The distal end of the catheter guide tube cuts into the endometrium causing it to bleed. With actual embryo transfer it has been shown that there is a not insignificant danger of injury to the embryos from the surface of the reinforcing tube. This can be put down to the relatively rough surface of the drawn metal reinforcing tube. Further, as a successful embryo transfer cannot be performed with an injured endometrium the success rate when using this known set of instruments must be regarded as extremely low.

With a set of instruments for uterine embryo transfer which differs from the above-mentioned type in that the catheter does not have a metal reinforcing tube but, on the contrary, the proximal area of which is stabilized through the use of only two flexible tubes arranged in a coaxial fashion, a catheter guide tube is provided with an acorn-shaped tip. This catheter guide tube can be inserted in the uterus using a flexible mandrin even without the necessity of prior shaping.

This means that, upon insertion into the uterus, the catheter guide tube is also relatively flexible and the danger of injuring the endometrium is reduced. On the other hand, there is the not low probability that just the acorn-shaped distal end of the catheter guide tube could penetrate and thereby injure the endometrium. Here it is especially the sharp edge between the tapering surface of the "acorn" and the outlet of the catheter which is significant. Of course, the omission of an actual reinforcing tube for the catheter is a disadvantage. Despite the two coaxial flexible tubes the catheter can bend under the weight of an attached syringe and thus be pulled out of the catheter guide tube in an uncontrolled manner with the likelihood of being damaged. Naturally, both of these possibilities are extremely undesirable when performing a uterine embryo transfer or intra-uterine insemination.

With the known set of instruments the catheter guide tube is provided with a movable stop in its distal area for positioning in the portio.

A set of instruments for transvaginal gamete transfer and for catheterization of the fallopian tubes has a catheter guide tube with a bend in the distal area, the distal end of which finishes in a ball. The bend is provided in order to make the insertion of the catheter guide tube into the entrance to the fallopian tubes easier. The ball centres the outlet for the catheter in the tube.

Teflon is known as a material for embryo transfer catheters and the associated catheter guide tubes. Teflon can be employed for the formation of smooth surfaces which are advantageous.

SUMMARY OF THE INVENTION

It is the object of the invention to demonstrate a set of instruments of the aforementioned type which is associated with a success rate for embryo transfer or insemination which is as high as possible.

According to the invention, this is achieved in that the catheter guide tube has a slight bend in its distal area, that the catheter guide tube has a ball on its distal end, and that the metal reinforcing tube surrounds the catheter. Surprisingly, it has been shown that a slight bend in the distal area of the catheter guide tube is also advantageous in a set of instruments for uterine embryo transfer or intrauterine insemination. This eases the entry of the catheter guide tube into the uterus. Therefore, as a result of this bend, a mandrin is totally unnecessary with the new set of instruments. The flexibility of the catheter guide tube is completely adequate to enable the desired end position to be reached and can be utilized to avoid injuries to the hyperflexio uteri or fissured cervical canal. Here also the ball-shaped attachment on the distal end of the catheter guide tube has a positive effect. The ball slides along over the endometrium with a minimal danger of injury. Moreover, the formation of a scraped edge between the outer surface and the inner surface of the catheter guide tube is essentially prevented through use of the ball. As a rule, the distal opening of the catheter guide tube for the catheter does not come into contact with the endometrium at all. Of course, the bent shape of the distal area also plays a part in this. However, also essential for the increase in the success rate when using the new set of instruments is the arrangement of the reinforcing tube around the catheter. The embryos do not come into contact with the drawn metal of the reinforcing tube. They slide along the smooth inner wall of the catheter without danger of injury.

The catheter guide tube can be constructed in one piece from Teflon and, in particular, with a flexible distal area. In this way a catheter guide tube can be constructed without extra effort as an item which is used only once but still corresponding to all necessary requirements.

The outside diameter of the ball can be more than two times, advantageously three or four times, the size of the inside diameter of the catheter guide tube at its distal opening. The ball, which is attached to the end of the catheter guide tube, must have a minimum size in order to be able to slide over the endometrium without injuring it. On the other hand, too large a diameter hinders the entry of the catheter guide tube into the uterus. Taking the normal outside diameter of a conventional catheter and the corresponding inside diameter of the catheter guide tube results in a ball diameter which is some three times the inside diameter of the catheter guide tube, an ideal end to the catheter guide tube.

The catheter can have a bend in its distal area which corresponds to the bend in the catheter guide tube. The additional bend in the catheter makes it easier to push it beyond the distal end of the bent catheter guide tube without risk of injury.

The catheter can have a scale in its proximal area which, in conjunction with the proximal opening of the catheter guide tube, indicates the position of the distal end of the catheter relative to the distal end of the catheter guide tube. In this way injury to the endometrium caused by a catheter which has been pushed too far beyond the ball of the catheter guide tube can be avoided.

The reinforcing tube can be made from special steel and firmly fixed in the syringe connection to the catheter. The syringe connection must, in any case, be rigidly connected to the flexible tube of the catheter. In doing this the uncomplicated support of the reinforcing tube can be carried out at the same time. The use of special steel for the reinforcing tube is simple and rules out any problems of corrosion.

The catheter can have a flexible tube made from polished synthetic material and can be rounded off at its distal end. The use of synthetic material for the flexible tube of the catheter guarantees its resistance to radiation, thereby rendering possible its sterilization using radiation. By contrast, articles made from Teflon disintegrate upon exposure to radiation. The polished surface of the synthetic material presents no danger to the outer skin of the embryos. Further, the rounded tip of the catheter serves to protect the endometrium.

A scale and a movable mark on the scale can be provided on the outside of the catheter guide tube in its distal area. The movable mark can be used as a stop at the portio in order to reach certain penetrating depths into the uterus with the catheter guide tube which can then be read from the scale. Advantageously, the mark is also suitable for indicating the direction of the bend. This allows the doctor using the set of instruments to also guide the catheter guide tube after the bend has been inserted into the uterus with some precision.

The catheter guide tube can have a connecting sleeve at its proximal end, whereby the catheter has a syringe connection with a counterpart for inserting into the connecting sleeve. Therefore, to ease handling, the catheter guide tube and the catheter can be joined together prior to insertion. Further, a connecting sleeve made from a soft synthetic material is, at the same time, an ideal gripping piece for the catheter guide tube.

The catheter guide tube can be provided with ball forceps for receiving a speculum in a holder. This enables precise positioning of the catheter guide tube with respect to the uterus, and allows the doctor using the set of instruments to keep his hands free for inserting the catheter, for example.

BRIEF DESCRIPTION OF THE DRAWINGS

The invention is more closely illustrated and described in the following by means of an embodiment example. It shows:

FIG. 1 is a side view of the catheter guide tube,

FIG. 2 is a side view of the catheter with the reinforcing tube, and

DETAILED DESCRIPTION

Figure 3:
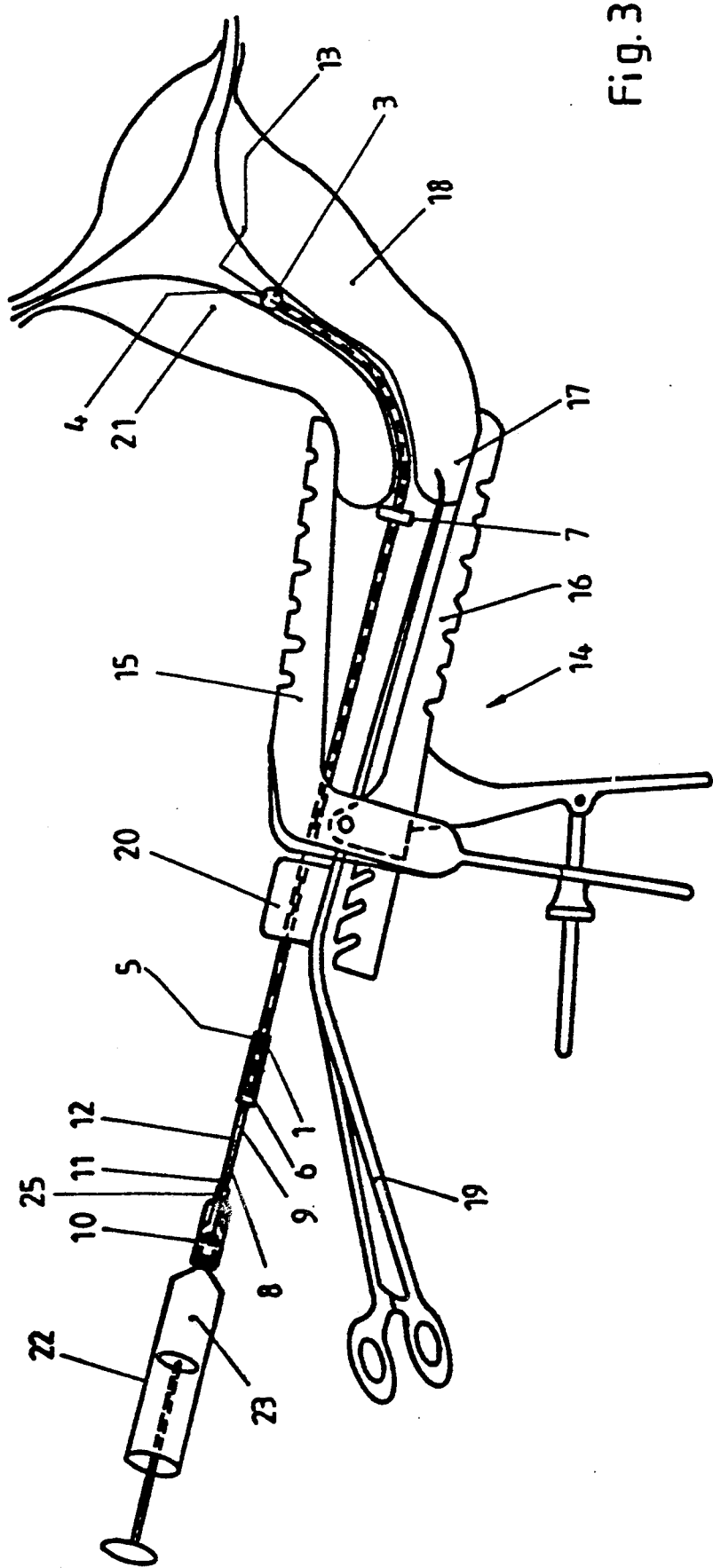
FIGS. 3 to 5 show the set of instruments in use.

The catheter guide tube shown in FIG. 1 has a slight bend 2 in its distal area and its distal end finishes with a ball 3. The outside diameter of ball 3 here is 3.5 times the inside diameter of the catheter guide tube 1 at its distal opening 4. The catheter guide tube 1 has a connecting sleeve 5 at its proximal end which, at the same time, forms a gripping piece for the catheter guide tube 1. The proximal opening 6 of the catheter guide tube 1 and/or the connecting sleeve 5 are funnel-shaped to ease the entry of the catheter. The catheter guide tube 1 is formed from flexible Teflon as one piece with the ball 3 but without the connecting piece 5. In this instance the catheter guide tube 1 exhibits particular flexibility in its distal area with the bend 2. The connecting piece 5 is made from a soft synthetic material which prevents sliding. In its distal area the catheter guide tube 1 has a scale 24 with a movable mark 7 on the scale. The mark 7 is intended as a stop and also indicates the direction of the bend 2. A mandrin for the catheter guide tube 1 is not normally provided.

The catheter 8 illustrated in FIG. 2 has a flexible tube 9 and a connection 10 for a syringe at its proximal end. The flexible tube 9 is made from polished synthetic material which allows an extremely smooth surface to be formed. The flexible tube 9 is surrounded by a reinforcing tube 11 in the proximal area of the catheter 8. Outside the reinforcing tube 11 in the distal area of the catheter 8 the flexible tube 9 is provided with a bend 26 similar to bend 2 of the catheter guide tube 1. The reinforcing tube 11 is made from drawn high-grade steel and fixed in the syringe connection 10 together with the flexible tube 9. In this case the reinforcing tube 11 does not form the inner surface of the catheter 8 at any point. The catheter 8, in its proximal area, has a scale 12 on the outside of the reinforcing tube 11. The scale 12 indicates, in conjunction with the proximal opening 6 of the catheter guide tube 1, the position of the distal end 13 of the catheter 8 relative to the distal opening 4 of the catheter guide tube 1 according to FIG. 1. The syringe connection 10 has a counterpart 25 for insertion in the connecting sleeve 5 of the catheter guide tube 1. The catheter 8, like the catheter guide tube 1 according to FIG. 1, is intended as a sterile, packed item which is to be used only once.

FIG. 3 shows the new set of instruments with the catheter guide tube 1 and the catheter 8 during uterine embryo transfer. A ball forceps 19, which grips onto and pulls forward the portio 17 of the uterus 18, is attached to a speculum 14, with upper arm 15 and lower arm 16, inserted into the vagina which is not illustrated here. A holder 20 is provided on the ball forceps 19. The catheter guide tube 1 is clamped into the holder 20. When the mark 7 stops at the portio 17 the catheter guide tube 1 projects about 4 cm into the uterus, whereby this amount can be adjusted by shifting the mark 7. The ball 3 on the distal end of the catheter guide tube 1 prevents injury to the endometrium 21 during insertion of the catheter guide tube 1 into the uterus 18. The surface of the ball 3 functions here as a broad support to the pushing force exerted by the doctor on the catheter guide tube 1. The bend 2 according to FIG. 1 is also a help during insertion of the catheter guide tube 1 into the uterus 18. The original bend 2 can no longer be identified in FIG. 3 because the catheter guide tube 1 has matched itself to the shape of the uterus 18. The catheter 8, inside the catheter guide tube 1, projects with its distal end 13 about 1 cm to 2 cm beyond the distal opening 4 at the ball 3 of the catheter guide tube 1, whereby this Figure again refers to a typical overall length of the uterus 18 of approximately 6.5 cm. The size of this projection can be read from the scale 12 opposite the proximal opening 6 of the catheter guide tube 1. A syringe 22 is placed in the syringe connection 10 of catheter 8. There is a fluid 23 in the syringe 22 which contains the embryo to be transferred. The reinforcing tube 11 safely prevents the flexible tube 9 of the catheter 8 from kinking under the weight of the syringe 22 or from being pulled out of the catheter guide tube 1.

The new set of instruments enables a clear increase in the success rate for uterine embryo transfers. The danger of injury to the endometrium 21 on the one hand, and the embryo being transferred on the other, are extremely low when using this set of instruments. Apart from that, the reinforcing tube 11 prevents unpleasant consequences resulting from carelessness on the part of the doctor performing the embryo transfer. The doctor can, therefore, concentrate fully on what is essential, i.e. the insertion of the catheter guide tube and the catheter itself without causing injury.

Figure 4:
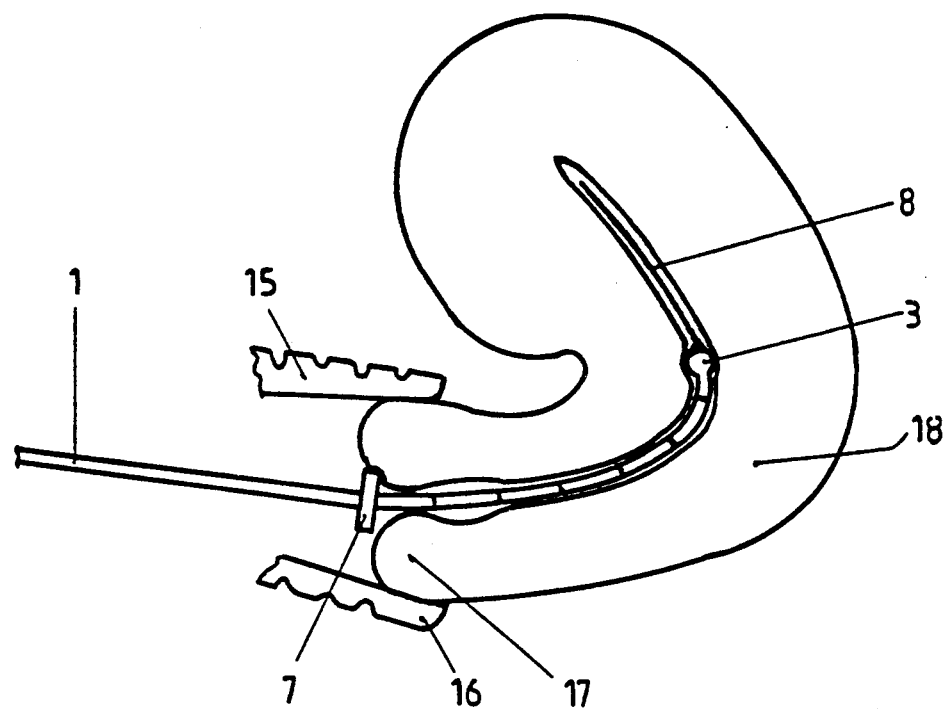

Surprisingly, the new set of instruments can be successfully employed in problem cases which are normally difficult to overcome. In FIG. 4 the inserted catheter guide tube 1 with projecting catheter 8 is shown for a case of hyperflexio uteri. The bends 2, 26 of the catheter guide tube 1 and the catheter 8 are the reason why the severly bent surfaces of the endometrium 21 are not injured or rather, that these severly bent surfaces of the endometrium 21 do not make it impossible to insert the catheter guide tube 1 and the catheter 8.

Figure 5:
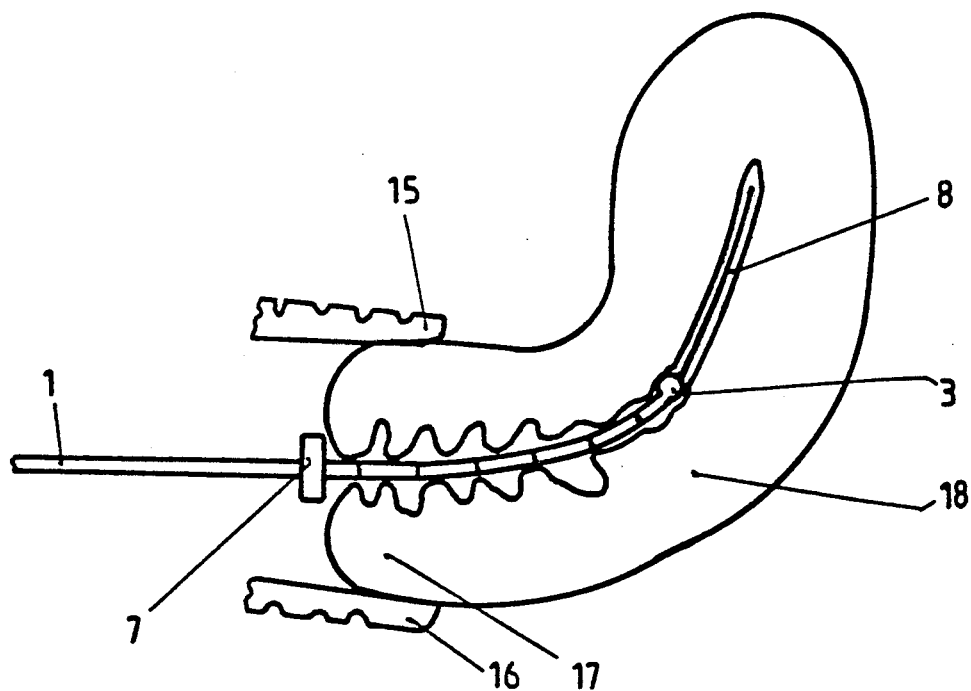

In FIG. 5 the problem case of a fissured cervical canal is illustrated. Here, the ball 3 and the bend 2 of the catheter guide tube are responsible for the fact that uterine embryo transfer or intra-uterine insemination can indeed be carried out.

It will be understood by persons skilled in the art that the foregoing description relates to a preferred embodiment of the invention, and that numerous variations and modifications may be made thereto without departing from the spirit and scope of the invention as set forth in the following claims.

We claim:

1. Set of instruments for uterine embryo transfer and intra-uterine insemination comprising a catheter guide tube (1) and a catheter (8) slidably movable within the catheter guide tube, the catheter having a proximal area and (8) being provided with a metal reinforcing tube (11) surrounding the catheter (8) in its proximal area, the catheter guide tube having a distal area and an open distal end and (1) including a slight bend (2) in its distal area and a ball (3) on its distal end, with said distal area being flexible.

2. Set of instruments according to claim 1, in which said catheter guide tube has an inside diameter and a distal opening (4) and the outside diameter of the ball (3) is at least two times the size of the inside diameter of the catheter guide tube (1) at its distal opening (4).

3. Set of instruments according to claim 1, characterized in that the catheter (8) has a bend (26) in its distal area corresponding to the bend (2) in the catheter guide tube (1).

4. Set of instruments according to claim 1, characterized in that the catheter (8) has a scale (12) in its proximal area which, in conjunction with the proximal opening (6) of the catheter guide tube (1), indicates the position of the distal end (13) of the catheter (8) relative to the distal opening of the catheter guide tube (1).

5. Set of instruments according to claim 1, characterized in that the reinforcing tube (11) is made from high grade steel and is fitted into the syringe connection (10) of the catheter (8).

6. Set of instruments according to claim 1, characterized in that the catheter (8) has a flexible tube (9) made from polished synthetic material and its distal end (13) is rounded off.

7. Set of instruments according to claim 1, characterized in that the catheter guide tube (1) has a scale in its distal area and a movable mark (7) is provided on the scale.

8. Set of instruments according to claim 1, characterized in that the catheter guide tube (1) has a connecting sleeve at its proximal end, and that the catheter has a syringe connection with a counterpart for inserting into the connecting sleeve.

9. Set of instruments according to claim 1, and further comprising a holder (20) for supporting the catheter guide tube (1), a ball forceps (19) for supporting the holder (20), and a speculum (14) for supporting the ball forceps (19).

10. Set of instruments according to claim 1, characterized in that the catheter guide tube is substantially straight from its proximal area for a majority of its length and is curved at its distal area.

* * * * *